United States Patent [19]

Samaritani et al.

[11] Patent Number: 5,650,390

[45] Date of Patent: Jul. 22, 1997

[54] GONADOTROPIN CONTAINING PHARMACEUTICAL COMPOSITIONS WITH SUCROSE STABILIZER

[75] Inventors: Fabrizio Samaritani; Patrizia Natale, both of Rome, Italy

[73] Assignee: Applied Research Systems ARS Holding N. V., Curacao, Netherlands Antilles

[21] Appl. No.: 244,575

[22] PCT Filed: Dec. 17, 1992

[86] PCT No.: PCT/IT92/00165

§ 371 Date: Jul. 28, 1994

§ 102(e) Date: Jul. 28, 1994

[87] PCT Pub. No.: WO93/11788

PCT Pub. Date: Jun. 24, 1993

[30] Foreign Application Priority Data

Dec. 18, 1991 [IT] Italy .................... RM91A0952

[51] Int. Cl.⁶ .................................................. A61K 31/18
[52] U.S. Cl. .................... 514/8; 514/53; 514/561; 562/575; 127/29
[58] Field of Search ................... 514/8, 53, 561; 127/29; 562/575

[56] References Cited

U.S. PATENT DOCUMENTS

| 3,637,640 | 1/1972 | Huber .................... 260/115 |
| 3,816,617 | 6/1974 | Banik .................... 424/100 |
| 5,128,453 | 7/1992 | Arpaia et al. .................... 530/398 |

FOREIGN PATENT DOCUMENTS

| 0388223 | 9/1990 | European Pat. Off. ......... A61K 3/38 |
| 0448146 | 9/1991 | European Pat. Off. ........ A61K 47/12 |
| 3520228 | 6/1984 | Germany .................. A61K 37/36 |
| 59-109862 | 6/1984 | Japan . |
| 8501959 | 5/1985 | WIPO .............. C12P 21/00 |
| 8810270 | 12/1988 | WIPO . |
| 8909610 | 10/1989 | WIPO .............. A61K 37/02 |
| 8910407 | 11/1989 | WIPO .............. C12N 15/00 |

OTHER PUBLICATIONS

Section Ch., Week 9025, Derwent Publications Ltd., London, GB; Class B04, AN 90-188387 & JP, A, 2 121 933 (Kagaku Shiryo Kenky) 9 May 1990 (abstract).

Section Ch., Week 8036, Derwent Publications Ltd., London, GB; Class B04, AN 80-623660 & DD, A 141 996 (Wolf I) 5 Jun. 1980 (abstract).

*Primary Examiner*—Gary Geist
*Assistant Examiner*—Rosalynd Williams

[57] ABSTRACT

Pharmaceutical compositions containing FSH, LH or hCG stabilized by means of a combination of sucrose and glycine. The formulation is particularly suitable for stabilizing a lyophilisate of recombinant gonadotropins.

16 Claims, No Drawings

GONADOTROPIN CONTAINING PHARMACEUTICAL COMPOSITIONS WITH SUCROSE STABILIZER

This application is a 371 of PCT/It92/00165, filed Dec. 17, 1992.

FIELD OF THE INVENTION

The present invention concerns gonadotropin containing pharmaceutical compositions. More precisely, it concerns compositions of sucrose-stabilized gonadotropins. The gonadotropins of the present invention comprise FSH (Follicle Stimulating Hormone), LH (Luteinizing Hormone) and hCG (Human Chorionic Gonadotropin).

BACKGROUND OF THE INVENTION

It is known that highly purified proteins are time-unstable and are stabilized, for instance, in admixture with saccharides, such as lactose and mannitol, or else with proteins and aminoacids, such as albumin and glycine. Other high-molecular-weight compounds, having a biological origin, as, for instance, the marine colloids, dextran and other polysaccharides and the phospholipids often work equally well. Anyway, since the gonadotropins of the present invention are administered parenterally, these excipients are not suited for an injectable composition because of their allergenicity or their insufficient solubility, in some cases because of their potential toxicity or a concourse of these effects.

The composition of lyophilised proteins is described in M. J. Pikal, BioPharm, October 1990, 25–30. There are reported examples of proteins, such as growth hormone and ribonuclease A, formulated by using stabilizing excipients such as mannitol, glycin, arginine and lactose.

In particular, the lyophilisation is described of proteins in the presence of various substances in their amorphous state, as sugars, which increase the collapse temperature and possible to obtain shorter lyophilisation times. However, it is not feasible, according to the author, to foresee a standard formulation for all the proteins, and the choice of the best formulation requires a remarkable selection work.

German patent DE 3520228 describes bioactive proteins such as lymphokines, interferons, TNF (Tumor Necrosis Factor), insulin, growth hormone, in formulations which are stabilized by means of polysaccharides comprising repetitive maltotriose units. The use of sucrose as a stabilizing agent is known, for instance, in a formulation of lyophilized orgotein, as described in U.S. Pat. No. 3,637,640. International patent application WO 89/10407 describes the formulation with sucrose of M-CSF (Macrophage-Colony Stimulating Factor); patent application WO 89/09610 describes, instead, formulations of TNF which have been stabilized with albumin, dextran, polyethylene glycol, 80 polysorbate PVP, lactose, trialose or even sucrose.

The injectable formulations of gonadotropins are obtained by a process which includes their lyophilisation in order to obtain a dry powder. Gonadotropins are highly liable to denaturization during the lyophilisation process and it is desirable to obtain stable formulations able to maintain a longer cycle life when they are stored at room temperature.

European Patent EP 448146 describes lyophilised gonadotropin containing preparations, which are stabilized by means of a dicarboxylic acid salt, as, for instance, citric acid, tartaric acid and aspartic acid. Gonadotropins which are found on the market are stabilized by means of saccharides, for instance hCG is stabilized by means of mannitol (Profasi®, SERONO) and FSH is stabilized by means of lactose (Metrodin®, SERONO).

SUMMARY OF THE INVENTION

We have now found that sucrose confers a better stability to the formulation of gonadotropins and in particular to the form of these glycoproteins which have been prepared by recombinant DNA technique.

The main object of the present invention is to provide a pharmaceutical composition comprising a solid intimate mixture of a gonadotropin, such as FSH, LH or hCG, and a stabilizing amount of sucrose, alone or in combination with other stabilizing agents.

A further object is to provide a process for the preparation of said pharmaceutical composition, the step of lyophilising an aqueous solution of the components. Another object is to provide a dosage form of said pharmaceutical composition comprising the said solid mixture hermetically closed in a sterile condition within a container suitable for storage before use and suitable for reconstitution of the mixture for injectable substances.

DETAILED DESCRIPTION OF THE INVENTION

Another object is to provide a solution for said solid mixture reconstituted into an injectable solution. In order to evaluate the excipient's effect on the stability of the active ingredients, various formulations of recombinant FSH containing 150 I.U. pro vial have been prepared with various excipients: lactose, sucrose, glycine, sucrose plus glycine, lactose plus albumin and lactose plus glycine. All the formulations have been prepared by dissolving the excipients in phosphate buffer at pH 7, except the formulation with lactose (10 mg) which has been dissolved into $H_2O$ for injection and adjusted at pH 6.4.

The samples have been stored at 45° C. and tested with a biological assay at fixed intervals of time. Tables 1 and 2 give the results of the tests effected on two different batches of recombinant FSH in the presence of different excipients, after 2 and 4 weeks for batch 1 (Tab. 1) and after 1 and 3 weeks for batch 2 (Tab. 2).

The biological tests have been performed in compliance with the regulations of the European Pharmacopœia and effected in duplicate. The tests for FSH and LH are reported in the "Menotropin" monography, whereas the test for hCG is reported in the "Chorionic Gonadotropin" monography.

The results show that the most stable formulations among those tested are those containing sucrose, i.e. formulations with sucrose alone and with sucrose plus glycine. Sucrose shows, surprisingly, to be an efficient stabilizing agent against the denaturization of the gonadotropins.

The stabilizing agents which are employed in the compositions of the present invention include, therefore, sucrose alone or in combination with other excipients, preferably aminoacids such as glycine. In particular, the stability has been studied of recombinant FSH and recombinant LH.

The gonadotropins produced according to the technique of recombinant DNA must be subjected to a high purification process in order to avoid contamination agents having a non-human origin and this high purity renders them less stable than the corresponding urinary gonadotropins.

The recombinant gonadotropins of the present invention have been prepared by expression in CHO (Chinese Hamster Ovary) cells, transformed with the corresponding recombinant DNA, according to the

TABLE 1

Batch 1 of recombinant FSH I.U.

| Excipient | Amount (mg) | Theoretical titer | T = 0 | 45° C. 2 weeks | 45° C. 4 weeks |
|---|---|---|---|---|---|
| Lactose | 10 | 167.31 | 129.0 | 139.0 | 104.0 |
| Lactose | 30 | 167.31 | 132.0 | 118.0 | 116.0 |
| Sucrose | 30 | 167.31 | 158.0 | 163.0 | 136.0 |
| Sucrose | 50 | 167.31 | 140.0 | 135.0 | 150.0* |
| Sucrose + Glycine | 20 + 10 | 167.31 | 144.0 | 143.0 | 186.0 |
| Lactose + Albumin | 20 + 3 | 167.31 | 127.0* | 134.0 | 128.0 |
| Glycine | 20 | 167.31 | 132.0 | 107.0 | — |
| Lactose + Glycine | 20 + 10 | 167.31 | 153.0 | 132.0 | 104.0 |

*valid only one assay

TABLE 2

Batch 2 of recombinant FSH 150 I.U.

| Excipient | Amount (mg) | Theoretical titer | T = 0 | 45° C. 1 week | 45° C. 4 weeks |
|---|---|---|---|---|---|
| Lactose | 10 | 155.08 | 163.0 | 121.0 | 103.0 |
| Lactose | 30 | 155.08 | 164.0 | 166.0 | 108.0 |
| Sucrose | 30 | 155.08 | 165.0 | 128.0 | 151.0 |
| Sucrose | 50 | 155.08 | 150.0 | 143.0 | 157.0 |
| Sucrose + Glycine | 20 + 10 | 155.08 | 160.0 | 152.0 | 185.0 |
| Lactose + Glycine | 20 + 3 | 155.08 | 172.0 | 136.0 | 101.0 |
| Glycine | 20 | 155.08 | 136.0 | 115.0* | 97.0* |
| Lactose + Albunin | 20 + 10 | 155.08 | 171.0* | 137.0 | 157.0 |

*valid only one assay technique described in European patents EP 160699 and EP 211894.

The close study of recombinant-FSH-containing formulations has been performed by using different compositions, according to the lay-out of Tab. 3, respectively comprising: a) lactose, b) sucrose, c) sucrose plus glycine.

The lyophilisate was prepared by diluting the bulk of gonadotropin with a solution of the excipient in water for injection ("a" formulation) or 0.01M phosphate buffer ("b" and "c" formulations) in order to achieve the concentration of 200 I.U./ml, adjusting the pH at 6.4 for the lactose-containing formulations and at 7 for the sucrose containing or sucrose-plus-glycin-containing formulations. The solution has been filtered, brought to the final volume with the remaining solution of the excipient in order to achieve the concentration of 150 I.U./ml and lyophilized.

The accelerated stability of these formulations has been studied so that the stability of the same can be foreseen when they are stored in containers at room temperature, through the extrapolation of the data obtained at higher temperatures (+37° C.; +45° C.; +50° C.).

The accelerated stability of the FSH formulations has been determined through the biological activity test, performed at the time intervals which are reported in the corresponding Tables.

Two ampoule preparations of HMG (Menotropin) were used as standard solutions, the first having a biopotency of 101.3 I.U. FSH/ampoule and 85.6 I.U. LH/ampoule, the second having a biopotency of 103.1 I.U. FSH/ampoule and 82.3 I.U. LH/ampoule. The samples, at

TABLE 3

Formulations of recombinant FSH

| Composition | Dosimetry I.U. | Lactose mg | Sucrose mg | Glycine mg | $Na_2HPO_4 \cdot 2H_2O$ mg | $NaH_2PO_4 \cdot H_2O$ mg |
|---|---|---|---|---|---|---|
| a | 150 | 10 | — | — | — | — |
| b | 150 | — | 30 | — | 1.11 | 0.45 |
| c | 150 | — | 20 | 10 | 1.11 | 0.45 | the concentrations 0.5; 1.0 and 2.0 I.U./ml, as well as the standard HMG solutions, were administered to three different groups of five rats each, through subcutaneous injection of 0.5 ml/rat twice a day for three consecutive days (final doses: 1.5; 3.0; 6.0 I.U. FSH/rat). Each animal further received altogether a dose of 40 I.U. hCG.

Data reported in Tab. 4 refer to formulations of 3 different batches of recombinant FSH, containing 150 I.U./ml FSH, in the presence of 10 mg lactose (Composition a), 30 mg sucrose (Composition b) and 20 mg sucrose plus 10 mg glycine (Composition c) in 5 ml vials. The tests were performed at the temperatures 37° C. 45° C. and 50° C.

The degradation was significant for the lactose containing formulations for all the test temperatures and for all the three batches. On the contrary, no appreciable variation was observed for the sucrose containing formulation of batch 1 at the same temperatures. For the formulation containing sucrose plus glycine relating to the first batch, the only appreciable degradation was observed at 50° C. For the formulations with sucrose or sucrose+glycine of the remaining batches, a degradation is observed which was lower anyway than that of the lactose containing formulation.

Tab. 5 gives further accelerated stability data, derived by the biological activity data, for 2 different batches (batch 1 and batch 2) of recombinant FSH formulations containing 150 I.U./ml FSH and 30 mg sucrose in 3 ml vials.

The study was performed on vials stored for 5 weeks at the temperature of 50° C. or for 10 weeks at the

TABLE 4

Study of the accelerated stability of recombinant FSH formulation (3 different batches - Batch 1, Batch 2 and Batch 3 containing 150 I.U./ml FSH) with lactose 10 mg (Composition a), sucrose 30 mg (Composition b) and sucrose (20 mg) + glycine (10 mg) (Composition c) in 5 ml vials.

Batch 1

| | | 50° C. | | | 45° C. | | | | | 37° C. | | |
|---|---|---|---|---|---|---|---|---|---|---|---|---|
| | T = 0 | 1 W | 3 W | 5 W | 2 W | 4 W | 8 W | 10 W | 11 W | 3 W | 5 W | 9 W | 12 W |
| a | 147 | 126 | 124* | 83 | 163* | 84 | 105 | 109 | — | 140* | 109 | 97 | 122* |
| b | 156 | 154 | 155 | 151 | 154 | 119 | 115 | — | 164 | 165 | 165 | 168 | 151 |
| c | 160 | 179 | 143 | 114 | 160 | 134 | 133 | 148 | — | 136 | 156* | 132 | 175 |

Batch 2

| | | 50° C. | | | 45° C. | | | | 37° C. | | | |
|---|---|---|---|---|---|---|---|---|---|---|---|---|
| | T = 0 | 1 W | 2 W | 5 W | 2 W | 6 W | 8 W | 10 W | 5 W | 7 W | 10 W | 12 W |
| a | 135 | 50* | 40* | — | 96* | 51 | 43 | — | 134 | 108 | 104 | 90 |
| b | 112 | 152* | 134 | 96 | 125 | 94 | 89 | 101 | 157 | 163 | 135 | 114* |
| c | 145 | 173* | 124 | 118 | 143 | 145 | 154 | 135 | 146 | 154 | 139 | 141 |

Batch 3

| | | 50° C. | | | 45° C. | | | | 37° C. | | | |
|---|---|---|---|---|---|---|---|---|---|---|---|---|
| | T = 0 | 1 W | 3 W | 5 W | 2 W | 4 W | 8 W | 10 W | 3 W | 5 W | 9 W | 12 W |
| a | 144 | 40* | 30* | — | 135 | 30* | 20* | — | 106 | 70 | 34 | — |
| b | 152 | 136 | 138 | 110 | 161 | 136 | 106 | 110 | 165 | 179 | 159 | 140 |
| c | 135 | 140 | 176 | 125 | 163 | 142 | 122 | 125 | 151 | 151 | 158 | 176 |

W = weeks
* = only one assay valid

TABLE 5

Study of the accelerated Stability of recombinant FSH formulations (105 I.U.) with sucrose (30 mg) in 3 ml vials

| | | 50° C. | | | | 45° C. | | | | 37° C. | | | |
|---|---|---|---|---|---|---|---|---|---|---|---|---|---|
| | T= 0 | 1 W | 2 W | 3 W | 5 W | 2 W | 4 W | 8 W | 10 W | 3 W | 5 W | 9 W | 12 W |
| Batch 1 | 141 | 135 | 113 | 136 | 140 | *135 | *149 | 179 | 166 | 147 | 145 | 149 | 122 |
| Batch 2 | 152 | 144 | 126 | 132 | *146 | 135 | 167 | 160 | 162* | 154 | 146 | 152 | 175 |

W = Weeks
*only one assay valid temperature of 45° C. or for 12 weeks at the temperature of 37° C. Again, no activity variation was observed at all the test temperatures for both batches.

The stability forecast at room temperature, given in Tab. 6 and extrapolated from the accelerated stability data of Tab. 5 according to the Garret's method (Garret E. R., J. Pharm. Sci., 51:811, 1962) shows a degradation of about 35% and 80% after two years of storage at 4° C. and 25° C. respectively for the lactose containing formulations.

No degradation is foreseen at 4° C. for the formulations with sucrose or sucrose plus glycine, whereas only a 6% decrease is foreseen for the sucrose containing formulations after two years at 25° C.

The stability has been studied of recombinant LH formulations (75 I.U.) with 50 mg sucrose (Composition a) and 50 mg lactose (Composition b). The exact composition of recombinant LH formulations is given in Table 7.

The study of the accelerated stability of such formulations stored at 37° C., 45° C. and 50° C., determined through the biological activity test measured in I.U. (Table 8) shows what has been already observed for the FSH formulations: the degradation of the sucrose containing preparations was extremely low, whereas the degradation of the lactose containing formulations was more evident.

The stability forecast at room temperature stability extrapolated from the accelerated stability data of Table 8 according to the Garret's method (Garret E. R., J. Pharm. Sci., 51:811, 1962) is given in Table 9.

A degradation is calculated of about 20% and 8% respectively for the lactose formulations stored for two

TABLE 6

Stability forecast of recombinant FSH formulations (150 I.U.) at room temperature

| | | Activity recovery (%) | | | |
|---|---|---|---|---|---|
| | | 4° C. | | 25° C. | |
| Composition | Excipient | 1 year | 2 years | 1 year | 2 years |
| a | Lactose | 79.30% | 62.89% | 41.57% | 17.28% |
| b | Sucrose | 99.61% | 99.22% | 96.86% | 93.82% |
| c | Sucrose + Glycine | no degradation | | no degradation | |

TABLE 7

Composition of recombinant LH formulations (75 I.U.) with sucrose 50 mg (Composition a) and lactose 50 mg (Composition b) in 3 ml vials

| Composition | Excipient | Amount (mg) |
|---|---|---|
| a | Sucrose | 47.75 |
| | $NaH_2PO_4.H_2O$ | 0.052 |
| | $Na_2HPO_4.2H_2O$ | 0.825 |
| b | Lactose | 50.00 |
| | $NaH_2PO_4.H_2O$ | 0.052 |
| | $Na_2HPO_4.2H_2O$ | 0.825 |

TABLE 8

Study of the accelerated stability of recombinant LH formulation (75 I.U.) in 3 ml vials

| Excipient | | 50° C. | | | |
|---|---|---|---|---|---|
| | mg | T = 0 | 1 W | 2 W | 5 W |
| Sucrose | 71 | 67* | 55 | 59 | |
| 47.75 | (58–86) | (34–121) | (42–73) | (47–76) | |
| Lactose | 77 | 57* | 34* | 40 | |
| 50 | (64–93) | (37–81) | (15–56) | (32–50) | |

| Ex-cipient | | 45° C. | | | | 37° C. | | |
|---|---|---|---|---|---|---|---|---|
| | mg | 2 W | 5 W | 8 W | 12 W | 6 W | 9 W | 12 W |
| Sucrose | 65 | — | 59 | 57 | 67* | 70* | 72 | |
| 47,75 | (50–85) | | (47–73) | (44–75) | (51–86) | (51–96) | (55–94) | |
| Lactose | 39 | 50* | 36* | — | 44* | 42* | 48 | |
| 50 | (29–52) | (33–79) | (20–57) | | (32–60) | (31–56) | (38–62) | |

*Only one assay valid
(In brackets the confidential limits)
W = weeks

TABLE 9

Stability forecast of recombinant LH formulations (75 I.U.) at room temperature

| Compositions | Excipient | Activity recovery % 4° C. | after 2 years 25° C. |
|---|---|---|---|
| a | Sucrose | 99.68% | 90.65% |
| b | Lactose | 80.56% | 19.86% | years at 4° C. and 25° C. The sucrose containing formulations remain unchanged for two years at 4° C. and a decrease of only 9% is calculated for the same formulations after two years at 25° C.

A study was also performed on urinary hCG formulations by using sucrose (formulation "a", 30 mg sucrose), lactose (formulation "b", 10 mg lactose) or mannitol (formulation "c", 20 mg mannitol) as stabilizers in 3 ml vials containing 500 I.U./vial hCG.

Tab. 10 gives the estimated values derived by the biological assay performed at different times for said hCG formulations stored at a temperature of 55° C.

Once again, sucrose is shown to be the most suited excipient in order to preserve hCG stability, i.e. an excipient which is much better than mannitol and better than lactose, even if, in this case, the stability difference for the three formulations is less strong with respect to the FSH or LH case.

EXAMPLES OF PHARMACEUTICAL MANUFACTURING

Materials: extra pure sucrose Ph Eur, BP, PH Nord, NF (Merck); lactose RPE ACS (Carlo Erba); glycine for analysis use (Merck), $NA_2HPO_4.2H_2O$ for analysis use (Merck), $NaH_2PO_4.H_2O$ RPE (Carlo Erba); 85% phosphoric acid RPE ACS (Carlo Erba); 0.1M NaOH (Merck); water for injectables.

As containers, 3 or 5 ml glass vials were used (type I borosilicate glass) with rubber fastener (Fradagrada Pettenati and Pharmagummi, butyl mixture) and aluminum ring.

Preparation of the Sucrose Containing Recombinant FSH Solution (for 1,200 Vials Containing Each 150 I.U. FSH)

Sucrose (36 g) $Na_2HPO_4.2H_2O$ (1.33 g) and $NaH_2PO_4.H_2O$ (0.54 g) were dissolved into water for

TABLE 10

Study of stability at 55° C. of hCG formulations (500 I.U.) with sucrose (a), lactose (b) and mannitol (c)

| Composition | T = 0 | 3 W | 6 W |
|---|---|---|---|
| a | 511 | 567 | 597 |
| | (390.1–670.2) | (407.0–788.7) | (452.2–789.4) |
| b | 534 | 355 | 428 |
| | (396.7–719.6) | (293.7–430.2) | (330.2–55501) |
| c | 449 | 332 | 244 |
| | (330.2–611.7) | (259.0–425.5) | (201.8–295.9) |

W = weeks (Between brackets confidential 95% limits)

injectables (1,200 ml) in order to obtain the starting sucrose solution. The bulk of recombinant FSH (180,000 I.U.) was diluted with the solution so that an FSH solution was obtained at 200 I.U./ml.

The pH of the FSH solution and of the residual sucrose solution was adjusted at 7 by means of 0.1M NaOH or $H_3PO_4$. The FSH containing solution was filtered through a Durapore 0.22 um sterile filter and brought to the final volume with the residual excipients solution filtered through the same Durapore filter. During the process the solution temperature was kept between 4° and 8° C.

Preparation of the Sucrose Containing Recombinant LH Solution (for 1,200 Vials Each Containing 75 I.U. LH)

Sucrose (57.3 g), $Na_2HPO_4.2H_2O$ (0.99 g) and $NaH_2PO_4.H_2O$ (0.62 g) were dissolved into water for injectables (600 ml) in order to obtain the starting sucrose solution. The recombinant LH bulk (90,000 I.U.) was diluted with the sucrose solution so that an LH solution is obtained at 300 I.U./ml.

The pH of the LH solution and of the residual sucrose solution was adjusted at 8 by means of 0.1M NaOH or $H_3PO_4$. The LH containing solution was filtered through a 0.22 um Durapore sterile filter and brought to the final volume by means of the residual excipients solution filtered through the same Durapore filter. During the process the solution temperature was kept between 4° and 8° C.

The solutions containing different excipients were prepared in a similar manner.

Filling Up and Lyophilisation 3 ml or 5 ml vials were filled with 1 ml of FSH solution or 0.5 ml of LH solution, transferred to the freeze-dryer and cooled at −45° C. for 6 hrs. at least. The lyophilisation was started at the temperature of −45° C. with a 0.07 vacuum. The heating was performed according to the following scheme: +20° C. for 20 hrs., then ±35° C. until the end of the cycle.

On the reconstituted solution the usual quality controls were performed. Although the present invention has been illustrated by means of specific examples, it is understood that variations can be introduced without departing from the spirit and scope of the invention.

We claim:

1. A pharmaceutical composition comprising a solid intimate mixture of gonadotropin and a stabilizing amount of sucrose in combination with glycine.

2. A pharmaceutical composition according to claim 1 wherein the sucrose is between 20 and 50 mg per unit dosage.

3. A pharmaceutical composition according to claim 1, wherein the solid intimate mixture is a lyophilisate.

4. A pharmaceutical composition according to claim 3, wherein the gonadotropin is FSH, or LH or hCG.

5. A pharmaceutical composition according to claim 1, wherein the gonadotropin is recombinant.

6. A pharmaceutical composition according to claim 1, containing 75 or 150 I.U. of FSH, 30 mg of sucrose, and an effective amount of glycine.

7. A pharmaceutical composition according to claim 1, containing 75 or 150 I.U. of LH, 47.75 mg of sucrose, and an effective amount of glycine.

8. A pharmaceutical composition according to claim 4, wherein the gonadotropin is recombinant.

9. A process for preparing a pharmaceutical composition according to claim 1 comprising preparing an aqueous solution of the components, distributing the components within containers, and drying or lyophilizing the solution within the containers.

10. A process according to claim 9, wherein the pH of the solution is within the range 6.5–8.5.

11. A process according to claim 10, wherein the pH of the solution is 7 for the FSH formulation and 8 for the LH formulation.

12. Forms of presentation of said pharmaceutical composition consisting essentially of the solid mixture according to claim 1, hermetically closed in a sterile condition in a container suited for storage before use and reconstitution of the mixture in a solvent or a solution for injectables.

13. A solution comprising the solid mixture according to claim 12, reconstituted in a solvent or a solution for injectables.

14. Forms of presentation of said pharmaceutical composition comprising the solid mixture according to claim 8, hermetically closed in a sterile condition in a container suited for storage before use and reconstitution of the mixture in a solvent or a solution for injectables.

15. Forms of presentation of said pharmaceutical composition comprising the solid mixture according to claim 1, hermetically closed in a sterile condition in a container suited for storage before use and reconstitution of the mixture in a solvent or a solution for injectables.

16. Forms of presentation of said pharmaceutical composition comprising the solid mixture according to claim 1, hermetically closed in a sterile condition in a container suited for storage before use and reconstitution of the mixture in a solvent or a solution for injectables, wherein the gonadotropin is FSH, LH or hCG.

* * * * *